US009993549B2

(12) United States Patent
Tokumoto et al.

(10) Patent No.: US 9,993,549 B2
(45) Date of Patent: Jun. 12, 2018

(54) ADJUVANT COMPOSITION, ADJUVANT PREPARATION CONTAINING SAME, AND KIT

(71) Applicant: HISAMITSU PHARMACEUTICAL CO., INC., Tosu-shi, Saga (JP)

(72) Inventors: Seiji Tokumoto, Tsukuba (JP); Kazuya Machida, Tsukuba (JP); Nao Kurokawa, Tsukuba (JP); Rie Namiki, Tsukuba (JP)

(73) Assignee: HISAMITSU PHARMACEUTICAL CO., INC., Toshu-Shi, Saga (JP)

( * ) Notice: Subject to any disclaimer, the term of this patent is extended or adjusted under 35 U.S.C. 154(b) by 0 days. days.

(21) Appl. No.: 15/032,718

(22) PCT Filed: Oct. 30, 2014

(86) PCT No.: PCT/JP2014/078958
§ 371 (c)(1),
(2) Date: Apr. 28, 2016

(87) PCT Pub. No.: WO2015/064710
PCT Pub. Date: May 7, 2015

(65) Prior Publication Data
US 2016/0263215 A1 Sep. 15, 2016

(30) Foreign Application Priority Data

Oct. 31, 2013 (JP) ................................ 2013-227166
Jan. 20, 2014 (JP) ................................ 2014-008089

(51) Int. Cl.
*A61K 39/39* (2006.01)
*A61K 9/08* (2006.01)
*A61K 9/00* (2006.01)
*A61K 47/10* (2017.01)
*A61K 9/70* (2006.01)
*A61K 39/00* (2006.01)

(52) U.S. Cl.
CPC .......... *A61K 39/39* (2013.01); *A61K 9/0014* (2013.01); *A61K 9/08* (2013.01); *A61K 9/7023* (2013.01); *A61K 39/0008* (2013.01); *A61K 47/10* (2013.01); *A61K 9/0021* (2013.01); *A61K 2039/54* (2013.01); *A61K 2039/55511* (2013.01)

(58) Field of Classification Search
CPC combination set(s) only.
See application file for complete search history.

(56) References Cited

U.S. PATENT DOCUMENTS

| 4,605,670 A | 8/1986 | Saito et al. |
|---|---|---|
| 4,659,611 A | 4/1987 | Iwase et al. |
| 4,863,970 A | 9/1989 | Patel et al. |
| 5,942,237 A | 8/1999 | Gizurarson et al. |
| 6,603,998 B1 | 8/2003 | King et al. |
| 6,818,222 B1 | 11/2004 | Barchfeld et al. |
| 2001/0006645 A1 | 7/2001 | Norton et al. |
| 2003/0039667 A1 | 2/2003 | Jira et al. |
| 2003/0045492 A1 | 3/2003 | Tang et al. |
| 2003/0099659 A1 | 5/2003 | Gizurarson et al. |
| 2003/0157155 A1 | 8/2003 | Lipp et al. |
| 2004/0024058 A1 | 2/2004 | Yamada et al. |
| 2004/0028698 A1 | 2/2004 | Colau et al. |
| 2004/0109869 A1 | 7/2004 | Glenn et al. |
| 2004/0185055 A1 | 9/2004 | Glenn et al. |
| 2005/0059740 A1 | 3/2005 | Graeber et al. |
| 2005/0106226 A1 | 5/2005 | Cormier et al. |
| 2005/0112135 A1 | 5/2005 | Cormier et al. |
| 2005/0163787 A1 | 7/2005 | Gizurarson et al. |
| 2006/0110433 A1 | 5/2006 | Terahara et al. |
| 2006/0183797 A1 | 8/2006 | Cohen et al. |
| 2007/0292461 A1* | 12/2007 | Tamarkin ................. A61K 8/86 424/401 |
| 2009/0130127 A1 | 5/2009 | Tokumoto et al. |
| 2010/0047327 A1* | 2/2010 | Kuwahara ............ A61K 9/0014 424/449 |
| 2011/0112509 A1 | 5/2011 | Nozaki et al. |
| 2012/0156258 A1 | 6/2012 | Tokumoto et al. |
| 2014/0037694 A1 | 2/2014 | Morimoto et al. |
| 2015/0071970 A1 | 3/2015 | Tokumoto et al. |

FOREIGN PATENT DOCUMENTS

| EP | 0 287 346 A1 | 10/1988 |
|---|---|---|
| EP | 0 623 287 A1 | 11/1994 |
| JP | S60-013721 A | 1/1985 |
| JP | S60-161918 A | 8/1985 |
| JP | H5-112466 A | 5/1993 |
| JP | H5-255112 A | 10/1993 |

(Continued)

OTHER PUBLICATIONS

Form PCT/IB/373 issued in international application No. PCT/JP2014/078958 issued May 3, 2016.
Form PCT/IB/237 issued in international application No. PCT/JP2014/078958 mailed Jan. 27, 2015.
Aungst, et al., "Comparison of the effects of various transmucosal absorption promoters on buccal insulin delivery", International Journal of Pharmaceutics, 53 (1989) 227-235.
Search report issued in European application No. EP 12 750 249.0 dated Jun. 22, 2016.
European Search Report dated Mar. 3, 2017 issued in corresponding European Application No. 14858381.8.
Celesti, et al., "The Single-Pass Perfused Rabbit Ear as a Model for Studying Percutaneous Absorption of Clonazepam. II. Influence of Hydrogel-Borne Propylene Glycol and Skin Pretreatment with Lauryl Alcohol", Meth Find Exp Clin Pharmacol, vol. 15, No. 1, pp. 49-56, 1993.
Songkro, "An overview of skin penetration enhancers: penetration enhancing activity, skin irritation potential and mechanism of action", Songklanakarin Journal of Science and Technology, vol. 31, No. 3, pp. 299-321, 2009.

(Continued)

*Primary Examiner* — Robert S Cabral
(74) *Attorney, Agent, or Firm* — Nath, Goldberg & Meyer; Joshua B. Goldberg; Tanya E. Harkins

(57) ABSTRACT

An adjuvant composition of the present invention contains lauryl alcohol and propylene glycol. Contents of the lauryl alcohol and the propylene glycol are 0.5 to 25% by mass and 8.0 to 99.5% by mass, relative to the total mass of the adjuvant composition, respectively. The lauryl alcohol is dissolved, and the adjuvant composition is used for transdermal or transmucosal administration.

14 Claims, No Drawings

(56) References Cited

FOREIGN PATENT DOCUMENTS

| | | |
|---|---|---|
| JP | H9-508614 A | 9/1997 |
| JP | H10-500662 A | 1/1998 |
| JP | 2001-509491 A | 7/2001 |
| JP | 2001-517233 A | 10/2001 |
| JP | 2002-512186 A | 4/2002 |
| JP | 2002-535100 A | 10/2002 |
| JP | 2003-509473 A | 3/2003 |
| JP | 2004-504120 A | 2/2004 |
| JP | 2004-083520 A | 3/2004 |
| JP | 2004-510747 A | 4/2004 |
| JP | 2004-526757 A | 9/2004 |
| JP | 2004-528900 A | 9/2004 |
| JP | 2004-529906 A | 9/2004 |
| JP | 2004-538048 A | 12/2004 |
| JP | 2007-516968 A | 6/2007 |
| WO | 93/025168 A1 | 12/1993 |
| WO | 95/022989 A1 | 8/1995 |
| WO | 98/033474 A1 | 8/1998 |
| WO | 98/042375 A1 | 10/1998 |
| WO | 99/053912 A1 | 10/1999 |
| WO | 00/044438 A1 | 8/2000 |
| WO | 01/021207 A2 | 3/2001 |
| WO | 01/076608 A1 | 10/2001 |
| WO | 01/87276 A1 | 11/2001 |
| WO | 02/007813 A1 | 1/2002 |
| WO | 02/028426 A1 | 4/2002 |
| WO | 02/074244 A2 | 9/2002 |
| WO | 02/083058 A2 | 10/2002 |
| WO | 02/085446 A2 | 10/2002 |
| WO | 02/085447 A2 | 10/2002 |
| WO | 2005/016440 A1 | 2/2005 |
| WO | 2005/074460 A2 | 8/2005 |
| WO | 2007/015441 A1 | 2/2007 |
| WO | 2008/093772 A1 | 8/2008 |
| WO | 2010/001671 A1 | 1/2010 |
| WO | 2010/013601 A1 | 2/2010 |
| WO | 2010/125470 A2 | 11/2010 |
| WO | 2010/143689 A1 | 12/2010 |
| WO | 2011/105508 A1 | 9/2011 |
| WO | 2012/115208 A1 | 8/2012 |
| WO | 2012/115222 A1 | 8/2012 |

OTHER PUBLICATIONS

Birinder Ghumman, Edward M. Bertram, and Tania H. Watts, "Chemical Chaperones Enhance Superantigen and Conventional Antigen Presentation by HLA-DM-Deficient as well as HLA-DM-Sufficient Antigen-Presenting Cells and Enhance IgG2a Production In Vivo", The American Association of Immunologists, 1998, p. 3262-p. 3270.

Marijana Stojanović, Irena Zivković, Aleksandra Inić-Kanada, Vladimir Petrusić, Mileva Mićić, and Ljiljana Dimitrijević, "The context of tetanus toxoid application influences the outcome of antigen-specific and self-directed humoral immune response", Microbiol Immunol, Feb. 2009 vol. 53, p. 89-p. 100.

Bruce J. Aungst, Nancy J. Rogers and Eli Shelter, "Enhancement of naloxone penetration through human skin in vitro using fatty acids, fatty alcohols, surfactants, sulfoxides and amides", International Journal of Pharmaceutics, 1986 vol. 33, p. 225-p. 234.

Daniel S Lyons, Stephanie A Lieberman, Johannes Hampl, J.Jay Boniface, Yueh-hsiu Chien, Leslie J Berg, Vlark M Davis, "A TCR Binds to Antagonist Ligands with Lower Affinities and Faster Dissociation Rates Than to Agonists", Immunity, Jul. 1996, vol. 5, p. 53-p. 61.

Junpeng Wang, Ligan Lu, Hongli Song, Yongjie Yang, Yuanfang Ma, "Effect of polyethylene glycol as adjuvant on hepatitis B virus DNA vaccine in vitro", Acta Microbiologica Sinica, 2010 vol. 50 No. 7, p. 949-p. 954.

Naruhito Higo, "Butsuriteki Keihi Kyushu Sokushinho Iontophoresis no kaihatsu Doko", Jounal of Pharmaceutical Science and Technology, vol. 65, No. 2, 2005, p. 93-p. 97.

Shoichi Harada et al, "I DDS Soron 5 Nippon Igai no Kuni de Jitsuyoka sareteiru DDS Seizai", DDS no Shinpo 1995-96, 1995.

Toshinobu Seki and Kazuhiro Morimoto, "Enhancing Effects of Medium Chain Aliphatic Alcohols and Esters on the Permeation of 6-Carboxyfluorescein and Indomethacin through Rat Skin", Drug Delivery, 2003, p. 289-p. 293.

E Galli, L Chini, S Nardi, N Benincori, P Panei, G Fraioli, V Moschese and P Rossi, "Use of a specific oral hyposensitization therapy to Dermatophagoides pteronyssinus in children with atopic dermatitis", Allergol. et Immunopathol, 1994, p. 18-p. 22.

Fulvio Mastrandrea, "The Potential Role of Allergen-Specific Sublingual Immunotherapy in Atopic Dermatitis", Am J Clin Dermatol vol. 5, No. 5, 2004, p. 281-p. 294.

F. Mastrandrea, G. Serio, M. Minelli, A. Minardi, G. Scarcia, G. Coradduzza and S. Parmiani, "Specific sublingual immunotherapy in atopic dermatitis. Results of a 6-year follow-up of 35 consecutive patients", Allergol Immunopathol vol. 28, No. 2, 2000, p. 54-p. 62.

Seong-Jun Park, Fumie Ohya, Kohei Yamashita, Koji Nishifuji and Toshiroh Iwasaki, "Comparison of Response to Immunotherapy by Intradermal Skin Test and Antigen-Specific IgE in Canine Atopy", Internal Medicine, 2000, p. 983-p. 988.

J. Ring, "Successful hyposensitization treatment in atopic eczema: results of a trial in monozygotic twins", British Journal of Dermatology, 1982 vol. 107, p. 597-p. 602.

A. Willemse, DVM; W.E. Van den Brom, PhD; A. Rijnberk, PhD, "Effect of hyposensitization on atopic dermatitis in dogs", JAVMA, May 15, 1984 vol. 184 No. 10, p. 1277-p. 1280.

Suzanne M. Abimosleh, Cuong D. Tran, and Gordon S. Howarth, "Emu Oil Reduces Small Intestinal Inflammation in the Absence of Clinical Improvement in a Rat Model of Indomethacin-Induced Enteropathy", Hindawi Publishing Corporation, 2013, p. 1-p. 10.

Valerie Ferro, Rosaria Costa, K. Christine Carter, Michael J.A. Harvey, Mary M. Waterston, Alexander B. Mullen, Christian Matschke, Jamie F.S. Mann, Angela Colston, William H. Stimson, "Immune responses to a GnRH-based anti-fertility immunogen, induced by different adjuvants and subsequent effect on vaccine efficacy", Elsevier Vaccine, 2004 vol. 22, p. 1024-p. 1031.

Füsun Acartürk, Ahmet Sencan, "Investigation of the effect of different adjuvants on felodipine release kinetics from sustained release monolithic films", International Journal of Pharmaceutics, 1996 vol. 131, p. 183-p. 189.

V. R. Sinha and Maninder Pal Kaur, "Permeation Enhancers for Transdermal Drug Delivery", Drug Development and Industrial Pharmacy, 2000 vol. 26 No. 11, p.1131-p. 1140.

ISR issued in international application No. PCT/JP2014/078958 dated Jan. 27, 2015.

* cited by examiner

ADJUVANT COMPOSITION, ADJUVANT PREPARATION CONTAINING SAME, AND KIT

This is a National Phase Application filed under 35 U.S.C. 371 as a national stage of PCT/JP2014/078958, filed Oct. 30, 2014, an application claiming the benefit of Japanese Application No. 2013-227166, filed Oct. 31, 2013 and Japanese Application No. 2014-008089, filed Jan. 20, 2014, the content of each of which is hereby incorporated by reference in its entirety.

TECHNICAL FIELD

The present invention relates to an adjuvant composition, an adjuvant preparation containing the same, and a kit.

BACKGROUND ART

Vaccines have recently been shifting from a live vaccine to an inactivated vaccine (all particles, a component, a vaccine, and the like) with the aim to improve the safety. The use of the inactivated vaccine reduces a risk such as infection, but on the other hand, may sometimes invite lowering of an immunologic response. In order to supplement the lowering of the immunologic response, the vaccine is often administered together with an adjuvant.

As a method for administering the adjuvant, subcutaneous administration, transdermal administration, transmucosal administration, and the like are known. The transdermal administration and the transmucosal administration are characterized by excellent convenience and safety, compared to the subcutaneous administration using an injection.

Patent Literatures 1 and 2 describe adjuvants for transdermal or transmucosal administration, which contain at least one member selected from aliphatic alcohols, free fatty acids and fatty acid derivatives but do not contain a specific bivalent unsaturated carboxylic acid ester. Patent Literature 3 describes an adjuvant for transdermal or transmucosal administration, which contains one or more members selected from the group glycerol, propylene glycol, polyethylene glycol, and triacetin, which are polyhydric alcohols or derivatives thereof.

CITATION LIST

Patent Literatures

Patent Literature 1: WO 2007/015441
Patent Literature 2: WO 2008/093772
Patent Literature 3: WO 2012/115222

SUMMARY OF INVENTION

Problems to be Solved by the Invention

When the adjuvant is transdermally or transmucosally administered, it is required to sufficiently suppress skin irritation. However, currently, the number of adjuvants which can be transdermally or transmucosally administrated with a good efficiency, sufficiently suppresses the skin irritation, and can be sufficiently exhibit an effect of potentiating the immunologic response, and particularly containing a low molecular weight compound, has not yet been small.

The present invention aims at providing an adjuvant composition for transdermal or transmucosal administration, which sufficiently suppresses the skin irritation and can exhibit the effect of potentiating the sufficient immunologic response.

Means for Solving the Problems

The present invention provides an adjuvant composition containing lauryl alcohol and propylene glycol, wherein contents of the lauryl alcohol and the propylene glycol are 0.5 to 25% by mass and 8.0 to 99.5% by mass, relative to the total mass of the adjuvant composition, respectively, wherein the lauryl alcohol is dissolved, and wherein the composition is used for transdermal or transmucosal administration.

The adjuvant composition sufficiently suppresses the skin irritation, and can exhibit the sufficient effect of potentiating the immunologic response. Please note that each component contained in the present invention is a known compound as an absorption accelerator in transdermal preparation. However, the effect obtained in the combination of the components described above in the present adjuvant composition is to potentiate the immunologic response of a subject, and an action mechanism and affecting effects thereof are quite different from those of the absorption accelerator in transdermal preparation. This can be confirmed by an event in which even when the present adjuvant composition is applied after a total amount of an injection of an antigen is administered, the effect of potentiating the immunologic response is obtained.

It is preferable that the adjuvant composition of the present invention further containing glycerol, wherein contents of the lauryl alcohol, the propylene glycol, and the glycerol are 0.5 to 25% by mass, 8.0 to 90% by mass, and 1.0 to 90% by mass, relative to the total mass of the adjuvant composition, respectively. When the glycerol is further contained and the contents of the lauryl alcohol, propylene glycol and glycerol are adjusted to the ranges described above, the effect of potentiating the immunologic response of the adjuvant composition can be further improved.

It is preferable that a ratio of the content of the propylene glycol to the content of the lauryl alcohol is from 1.0 to 99. When the contents of the lauryl alcohol and propylene glycol are adjusted to the ranges described above, a sufficient amount of the lauryl alcohol can be dissolved.

It is preferable that a ratio of the content of the propylene glycol to the content of the glycerol is from 0.4 to 99. When the contents of the glycerol and propylene glycol are adjusted to the ranges described above, a sufficient amount of the lauryl alcohol can be dissolved.

In addition, the present invention also provides an adjuvant preparation containing the adjuvant composition.

The adjuvant preparation contains the adjuvant composition described above, and thus the skin irritation is sufficiently suppressed, and the sufficient effect of potentiating the immunologic response can be exhibited.

A content of the adjuvant composition may be 50 to 100% by mass relative to the total mass of the adjuvant preparation. When the content of the adjuvant composition is within the range described above, the effect of potentiating the immunologic response of the adjuvant preparation can be further improved.

The adjuvant preparation can be an ointment, a cream, a gel, a suppository, a hydrogel patch preparation, a patch preparation, a lotion, a solution, an impregnated-type preparation, or a blister.

The patch preparation may be a matrix-type tape preparation, a laminated-type tape preparation, or a reservoir-type patch preparation. According to such a patch preparation, the adjuvant composition can be administered more quickly over a long period of time.

The adjuvant composition may be administered to a skin or a mucous membrane by microneedle puncture, needle-free injection, skin abrading, or mucous membrane abrading.

At least a part of the microneedle may be coated with the adjuvant composition that may administrated to a skin or a mucous membrane by puncture.

The adjuvant composition may be administered by iontophoresis, sonophoresis, or electroporation.

It is possible that the adjuvant preparation be administrated to an intact skin, an intact mucous membrane, a skin that had been subjected to physical or chemical treatment, or a mucous membrane that had been subjected to physical or chemical treatment.

The physical or chemical treatment may be at least one treatment selected from the group consisting of a heat-treatment, an ultrasonic treatment, an electric field treatment, a magnetic field treatment, a pressure treatment, an alkali treatment, a laser irradiation, an abrading treatment, and a microneedle treatment. When the skin or mucous membrane is subjected to such a treatment, the efficiency of the transdermal or transmucosal administration of the adjuvant preparation can be further improved.

The adjuvant preparation may be administered to the skin or mucous membrane either before the administration of an antigen or after the administration of an antigen.

The present invention provides also a kit containing the adjuvant composition described above or the adjuvant preparation described above.

The kit may further include an apparatus for an antigen or an antigen administration.

The present invention can also provide an immunostimulation method wherein a subject is an individual necessary for promotion of an immunoreaction. For example, the present invention provides an immunostimulation method containing the step of: transdermally or transmucosally administrating the adjuvant composition described above or the adjuvant preparation described above to human.

Effects of the Invention

The present invention can provide an adjuvant composition for transdermal or transmucosal administration, which sufficiently suppresses skin irritation and can exhibit a sufficient effect of potentiating the immunologic response.

The present invention can also provide an adjuvant preparation containing the adjuvant composition. Such an adjuvant preparation contains the adjuvant composition according to the present invention, and thus skin irritation is sufficiently suppressed and a sufficient effect of potentiating the immunologic response can be exhibited. In addition, the adjuvant preparation according to the present invention can contain the adjuvant composition described above in a high concentration, and thus an effect of potentiating the immunologic response upon the administration to the skin or mucous membrane is excellent. Further, the present invention can also provide a kit containing the adjuvant composition or the adjuvant preparation. Furthermore, the present invention can also provide an immunostimulation method containing the step of: transdermally or transmucosally administrating the adjuvant composition or the adjuvant preparation to an individual necessary for promotion of immunoreaction.

EMBODIMENTS FOR CARRYING OUT THE INVENTION

Preferable embodiments of the present invention are explained in detail. The present invention, however, is not limited to the embodiments described below.

The adjuvant composition for transdermal or transmucosal administration according to the present embodiment is an adjuvant composition containing lauryl alcohol and propylene glycol, wherein contents of the lauryl alcohol and the propylene glycol are 0.5 to 25% by mass and 8.0 to 99.5% by mass relative to the total mass of the adjuvant composition, respectively, and wherein the lauryl alcohol is dissolved. "The lauryl alcohol is dissolved" in the instant specification means to obtain evaluation A or B in Experimental Example 1 described below, preferably to obtain evaluation A.

The adjuvant composition having the components described above can be transdermally or transmucosally administrated, sufficiently suppresses the skin irritation, and can exhibit the excellent effect of potentiating the immunologic response (immunostimulation effect). The skin irritation is further suppressed, compared to a conventional impregnated-type preparation, which is directly applied to the skin, and the immunostimulation effect can be safely obtained. The effects above can be confirmed by measuring an immuno IgG antibody titer.

The reason in which the effects above can be obtained is unclear, but it can be considered that Langerhans' cells, existing in the skin or mucous membrane, are activated by transdermally or transmucosally administrating the adjuvant composition according to the present embodiment containing both the pre-determined amount of the lauryl alcohol and the pre-determined amount of the propylene glycol, and signals are efficiently transmitted to helper T (TH) cells existing in lymph nodes, whereby a high immunologic response can be obtained.

The adjuvant composition according to the present embodiment can exhibit the effect of potentiating the immunologic response by itself, and thus it is not necessary to mix with an antigen and then to administrate, and the composition can be administrated separately from the antigen. The excellent effect of potentiating the immunologic response can be preferably obtained by transdermal or transmucosal administration independently from the administration of the antigen. The administration of the adjuvant composition may be performed at any time of before the administration of the antigen, the same time upon the administration of the antigen, or after the administration of the antigen administration. It is preferable to perform it before or after the administration of the antigen administration. The administration mode of the adjuvant composition can be different from that of the administration of the antigen, and the adjuvant composition may be administrated in a route independent route from that of the antigen. It is not necessary, accordingly, to consider conditions of the antigen such as an administration amount thereof, when the adjuvant composition is administrated, an administration amount, an administration time, an administration mode of the adjuvant composition itself can be selected. The adjuvant composition according to the present embodiment can be administered separately the antigen, and thus the adjuvant composition can be administered avoiding swellings or pain, caused on the administrated site upon the administration of the antigen.

The content of the lauryl alcohol may be from 0.5 to 60% by mass relative to the total mass of the adjuvant composition, and is preferably from 0.5 to 25% by mass, more preferably from 1.0 to 20% by mass. When the content of the lauryl alcohol is adjusted to 60% by mass or less, the skin irritation caused by the adjuvant composition can be sufficiently suppressed. When the content of the lauryl alcohol is adjusted to 0.5% by mass or more, the effect of potentiating the immunologic response of the adjuvant composition can be sufficiently obtained. The content of the lauryl alcohol may be from 0.5 to 60% by mass, from 0.5 to 50% by mass, from 0.5 to 45% by mass, from 0.5 to 40% by mass, from 0.5 to 25% by mass, or from 0.5 to 20% by mass relative to the total mass of the adjuvant composition if the content is within the range described above. The content of the lauryl alcohol may also be from 1.0 to 25% by mass or from 1.0 to 20% by mass relative to the total mass of the adjuvant composition if the content is within the range described above.

The content of the propylene glycol is from 8.0 to 99.5% by mass relative to the total mass of the adjuvant composition, preferably from 40 to 99% by mass, more preferably from 49 to 99% by mass. When the content of the propylene glycol is adjusted to 8.0% by mass or more, the lauryl alcohol can be sufficiently dissolved. The content of the propylene glycol may be from 8.0 to 99.5% by mass, from 40 to 99.5% by mass, or from 49 to 99.5% by mass relative to the total mass of the adjuvant composition if the content is within the range described above. The content of the propylene glycol may also be from 8.0 to 99% by mass, from 40 to 99% by mass, or from 49 to 99% by mass relative to the total mass of the adjuvant composition if the content is within the range described above.

The adjuvant composition according to the present embodiment may further contain glycerol. When the glycerol is contained, the effect of potentiating the immunologic response of the adjuvant composition can be further improved.

When the adjuvant composition contains the glycerol, the content of the propylene glycol is preferably from 8.0 to 90% by mass, more preferably from 49 to 90% by mass, even more preferably from 49 to 79% by mass relative to the total mass of the adjuvant composition. When the content of the propylene glycol is adjusted to the range above, the lauryl alcohol can be more sufficiently dissolved. The content of the propylene glycol in the case in which the adjuvant composition contains the glycerol may be from 8.0 to 90% by mass or from 49 to 90% by mass relative to the total mass of the adjuvant composition if it is within the range described above. The content of the propylene glycol in the case in which the adjuvant composition contains the glycerol may also be from 8.0 to 79% by mass or from 49 to 79% by mass relative to the total mass of the adjuvant composition if it is within the range described above.

The content of the glycerol is preferably from 1.0 to 90% by mass, more preferably from 1.0 to 80% by mass, even more preferably from 8.0 to 60% by mass, particularly preferably from 16 to 50% by mass relative to the total mass of the adjuvant composition. When the content of the glycerol is adjusted to the range above, the lauryl alcohol can be more sufficiently dissolved. The content of the glycerol may be from 1.0 to 90% by mass, from 1.0 to 80% by mass, from 1.0 to 60% by mass, or from 1.0 to 50% by mass relative to the total mass of the adjuvant composition if the content is within the range described above. The content of the glycerol may also be from 8.0 to 90% by mass, from 8.0 to 80% by mass, from 8.0 to 60% by mass, or from 8.0 to 50% by mass relative to the total mass of the adjuvant composition if the content is within the range described above. The content of the glycerol may also be from 16 to 90% by mass, from 16 to 80% by mass, from 16 to 60% by mass, or from 16 to 50% by mass relative to the total mass of the adjuvant composition if the content is within the range described above.

A ratio of the propylene glycol content to the lauryl alcohol content is preferably from 1.0 to 99, more preferably from 2.8 to 89, even more preferably from 2.8 to 79. The ratio of the propylene glycol content to the lauryl alcohol content may be from 1.0 to 99, from 1.0 to 89, or from 1.0 to 79 if the ratio above is within the range described above. The ratio of the propylene glycol content to the lauryl alcohol content may also be from 2.8 to 99, from 2.8 to 89, or from 2.8 to 79 if the ratio above is within the range described above.

A ratio of the propylene glycol content to the glycerol content is preferably from 0.4 to 99, more preferably from 0.4 to 9.0, even more preferably from 0.6 to 9.0, particularly preferably from 1.0 to 4.0. The ratio of the propylene glycol content to the glycerol content may be from 0.4 to 99, from 0.4 to 9.0, or from 0.4 to 4.0 if the ratio is within the range described above. The ratio of the propylene glycol content to the glycerol content may also be from 0.6 to 99, from 0.6 to 9.0, or from 0.6 to 4.0 if the ratio is within the range described above. The ratio of the propylene glycol content to the glycerol content may also be from 1.0 to 99, from 1.0 to 9.0, or from 1.0 to 4.0 if the ratio is within the range described above.

The contents of the lauryl alcohol, the propylene glycol, and the glycerol in the adjuvant composition can be decided by collecting a pre-determined amount of the adjuvant composition, and determining the quantities thereof according to, for example, a gas chromatography. The measurement conditions may be set as follows:

Apparatus: GC-2010 manufactured by Shimadzu Corporation
Detector: Hydrogen flame ionization detector FID-2010 manufactured by Shimadzu Corporation
Column: GC column DB-1 manufactured by Agilent Ltd.
Carrier gas: He The adjuvant composition may contain other components if necessary. The other component may include aliphatic alcohols (provided that lauryl alcohol, glycerol, and propylene glycol are excluded), fatty acid derivatives, free fatty acids, fatty acid ethers, and the like.

As the component described above, for example, a compound represented by the following general formula (I) may be used.

$$CH_2R^1(CHR^2)_nCH_2R^3 \quad\quad\quad (I)$$

In the general formula (I) described above, $R^1$, $R^2$, and $R^3$ represent each independently H, OH, or $OCOR^4$; n is 0, 1, or 2 and when n is 2, $R^2$ may be the same or different; $R^4$ is a linear or branched alkyl group having 1 to 3 carbon atoms, a linear or branched alkenyl group having 2 or 3 carbon atoms, or an alkynyl group having 2 or 3 carbon atoms, provided that $R^1$, $R^2$, and $R^3$ are not H at the same time, and when n is 1, two or more of $R^1$, $R^2$, and $R^3$ are not OH at the same time.

As the aliphatic alcohol, in addition to the aliphatic alcohol represented by the general formula (I), linear or branched aliphatic alcohols may be used, but the linear aliphatic alcohols are preferable. The aliphatic alcohol may be any one of a saturated alcohol and an unsaturated alcohol, but the saturated aliphatic alcohol is preferable. Both of the number of carbon atoms and the molecular weight of the aliphatic alcohol are not limited, but aliphatic alcohols having 8 to 20 carbon atoms are more preferable. The case in which the number of carbon atoms is adjusted to the range described above is preferable in terms of the skin permeation.

The aliphatic alcohol may include, for example, octyldodecanol, oleyl alcohol, isostearyl alcohol, decanol, and the like. Of these aliphatic alcohols, octyldodecanol and isostearyl alcohol are preferable.

As the fatty acid derivative, in addition to the fatty acid derivative represented by the general formula (I), compounds having a fatty acid part may be used. The fatty acid derivative may include fatty acid esters, fatty acid amides, fatty acid halides, and the like. As the fatty acid derivative, fatty acid esters are preferable, and fatty acid esters having 10 to 20 carbon atoms in the fatty acid part and having an unsaturation of fatty acid of 0 or 1, and monovalent fatty acid esters are more preferable.

The fatty acid ester may include, for example, triacetin, sorbitan monolaurate, propylene glycol monolaurate, sorbitan monooleate, isopropyl myristate, polyethylene glycol, grycerol monooleate, cetyl palmitate, oleyl oleate, and the like. Of these fatty acid esters, sorbitan monolaurate is most preferable.

As the free fatty acid, linear or branched free fatty acids may be used. The acid may be any one of saturated and unsaturated free fatty acids. Free fatty acids having 8 to 20 carbon atoms are preferable. The case in which the number of carbon atoms is adjusted to the range described above is preferable in terms of the skin permeation.

The free fatty acid may include, for example, oleic acid, linolic acid, γ-linolenic acid, α-linolenic acid, lauric acid, stearic acid, palmitic acid, and the like. Of these free fatty acids, oleic acid and lauric acid are preferable.

The fatty acid ester may be any of ether compounds having a low molecular weight and ether compounds having a high molecular weight. Such an ether compound may include, for example, polyethylene glycol, and the like. As the polyethylene glycol, polyethylene glycol having an average molecular weight of 200 to 4000 is preferable, and polyethylene glycol having an average molecular weight of 200 to 1000 are more preferable. Such a polyethylene glycol is commercially available, for example, as a trademark Macrogol 400 (manufactured by Sanyo Chemical Industries Ltd.).

The aliphatic alcohols, the fatty acid derivatives, the free fatty acids, and the fatty acid ethers may be used alone or as a mixture of two or more kinds.

The adjuvant composition may be used as an adjuvant preparation containing the same.

Although a content of the adjuvant composition in the adjuvant preparation may be adjusted depending on the application thereof, and the like, it is preferable that the adjuvant composition is contained in a high concentration. The content of the adjuvant composition may be adjusted to from 50 to 100% by mass relative to the total mass of the adjuvant preparation, preferably from 75 to 100% by mass, more preferably from 85 to 100% by mass, even more preferably from 95 to 100% by mass. When the content of the adjuvant composition is adjusted to 50% by mass or more, the immunostimulation effect of the adjuvant preparation can be improved.

The adjuvant preparation may contain other components according to the application purpose, the mode of the preparation, and the like. The other components may include a thickener, a wetting agent, a filler, a solubilizer, a solubilizing agent, an absorption accelerator, a medicinal adjuvants, a stabilizing agent, an antioxidant, an emulsifier, a surfactant, a cross-linking agent, a polymerization agent, an adhesive, a plasticizer, a pH regulator, a preservative, an excipient, and the like.

As the thickener, thickeners capable of stably holding water in a content of 30 to 80%, and having water holding property are preferable. The thickener may include, for example, water-soluble polymers, e.g., natural polymers including plant polymers such as guar gum, locust bean gum, carrageenan, alginic acid, sodium alginate, agar, gum arabic (acacia gum), tragacanth gum, karaya gum, pectin, and starch; microbiological polymers such as xanthan gum; and animal polymers such as gelatin and collagen; semisynthetic polymers including cellulose polymers such as methyl cellulose, ethyl cellulose, hydroxyethyl cellulose, and sodium carboxymethylcellulose; soluble starch, carboxymethyl starch, and dialdehyde starch; synthetic polymers including vinyl polymers such as polyvinyl alcohol, polyvinylpyrrolidone and polyvinyl methacrylate; and acrylic polymers such as polyacrylic acid and sodium polyacrylate; polyethylene oxide, a methyl vinyl ether/maleic anhydride copolymer, and the like. Of these thickeners, the sodium polyacrylate is preferable. The sodium polyacrylate has a high gel strength, and an excellent water holding property. The sodium polyacrylate has more preferably an average degree of polymerization of 20000 to 70000. When the average degree of polymerization is more than 20000, a thickening effect is more sufficient, and the gel strength tends to be increased. When the average degree of polymerization is less than 70000, the lowering of workability, caused by too strong thickening effect, can be suppresses. When two or more kinds of the thickeners are used, for example, the sodium polyacrylate forms a polymer complex with a strong ion polymer, whereby an elastic gel having a higher gel strength can be obtained.

As the wetting agent, a polyhydric alcohols such as sorbitol may be used. As the filler, kaolin, zinc oxide, talc, titanium, bentonite, aluminum silicate, titanium oxide, zinc oxide, aluminum metasilicate, calcium sulfate, calcium phosphate, or the like may be used. A blending amount of the wetting agent and the filler added is preferably from 0.1 to 30% by mass, more preferably from 0.1 to 20% by mass relative to the total mass of the adjuvant preparation.

As the solubilizing agent or the absorption accelerator, propylene carbonate, crotamiton, 1-menthol, mint oil, limonene, diisopropyl adipate, or the like may be used.

As the medicinal adjuvants, methyl salicylate, glycol salicylate, 1-menthol, thymol, mint oil, nonylic acid vanillylamide, Capsicum extract, aluminum hydroxide, aluminum phosphate, aluminum chloride, aluminum hydroxyphosphite sulfate, or the like may be used.

As the surfactant, any of non-ionic surfactants and ionic surfactants (cationic, anionic, and amphoteric surfactants) may be used. It is desirable to use non-ionic surfactants which are usually used as a substrate for a medicine in terms of the safety. The surfactant may include, for example, sugar alcohol fatty acid esters such as sucrose esters of fatty acid; sorbitan fatty acid esters, glycerol fatty acid esters, polyglycerol fatty acid esters, propylene glycol fatty acid esters, polyoxyethylene sorbitan fatty acid esters, polyoxyethylene glycerol fatty acid esters, polyethylene glycol fatty acid esters, polyoxyethylene castor oil, polyoxyethylene hardened castor oil, and the like.

The adjuvant preparation may contain the cross-linking agent, the polymerization agent, and the like. When the preparation contains the components above, the ointment can be strengthened and can have the water holding property. The cross-linking agent and the polymerization agent are appropriately selected according to the kind of the thickener, and the like.

For example, when the polyacrylic acid or the polyacrylic acid salt is used for the thickener, in addition to a compound having at least two epoxy groups in the molecule, for example, a polyvalent metal compound is preferably used, for example, an inorganic acid salt such as chloride, sulfate, phosphate or carbonate; or an organic acid salt such as citrate, tartrate, gluconate, or stearate of Ca, Mg, or Al; an oxide such as zinc oxide or silicic anhydride; or a hydroxide such as aluminum hydroxide or magnesium hydroxide.

When the polyvinyl alcohol is used for the thickener, adipic acid, thioglycollic acid, an epoxy compound (epichlorohydrin), aldehydes, an N-methylol compound, a complex compound of Al, Ti, Zr, Sn, V, Cu, B or Cr, and the like are preferably used.

When the polyvinylpyrrolidone is used for the thickener, a methyl vinyl ether/maleic anhydride copolymer, a polyacid compound or alkali metal salt thereof (polyacrylic acid or tannic acid, and a derivative thereof), and the like are preferably used.

When the polyethylene oxide is used for the thickener, peroxide and polysulfone azide are preferably used.

When the methyl vinyl ether/maleic anhydride copolymer is used for the thickener, a polyfunctional hydroxy compound, polyamine, iodine, gelatin, polyvinylpyrrolidone, and a salt of iron, mercury or lead are preferably used.

When the gelatin is used for the thickener, aldehydes such as formaldehyde, glutaraldehyde, and dialdehyde starch; diepoxides such as glyoxal and butadiene oxide; diketones such as divinyl ketone, diisocyanates, and the like are preferably used.

When the sodium polyacrylate is used for the thickener, it is preferable to use, as the cross-linking agent, polyvalent metal salts such as lithium hydroxide, zinc hydroxide, aluminum hydroxide, and sodium borate. The zinc salts and aluminum salts are particularly preferable, because the cross-linking reaction is promoted.

A concentration of the polyvalent metal salt added as the cross-linking agent is preferably from 0.5 to 1.5 equivalents per equivalent of the thickener (or the water-soluble polymer). When the concentration of the polyvalent metal salt is adjusted to 0.5 equivalents or more, the reaction is promoted, and the gel strength is increased; whereas, when the concentration of the polyvalent metal salt is adjusted to 1.5 equivalents or less, the reaction is performed at an appropriate speed, whereby the gelation is uniformly performed and the workability can be improved.

As the adhesive, acrylic polymers and rubber polymers are preferable.

The acrylic polymer is not particularly limited so long as it is a copolymer containing at least one (meth)acrylic acid derivative including 2-ethylhexyl acrylate, methyl acrylate, butyl acrylate, hydroxyethyl acrylate or 2-ethylhexyl methacrylate, or the like. Copolymers containing 50% or more of 2-ethylhexyl acrylate are preferable. Specifically, as the specific adhesive may be used an acrylic acid/octyl acrylate copolymer, a 2-ethylhexyl acrylate/vinyl pyrolidone copolymer solution, a acrylate/vinyl acetate copolymer, a 2-ethylhexyl acrylate/2-ethlhexyl methacrylate/dodecy methacrylate copolymer, a methyl acrylate/2-ethylhexyl acrylate copolymer resin emulsion; a pressure sensitive adhesive such as an acrylic polymer contained in acrylic resin alkanolamine solution, a DURO-TAK acrylic pressure-sensitive adhesive agent series (manufactured by Henkel Ltd.), Eudragit series (manufactured by HIGUCHI INC.), or the like, which are described as the adhesive on "Pharmaceutical Additives Dictionary 2000" (edited by International Pharmaceutical Excipients Council Japan), and the like. As the rubber polymer, a styrene-isoprene-styrene block copolymer (hereinafter which is abbreviated to SIS), isoprene rubber, polyisobutylene (hereinafter which is abbreviated to PIB), a styrene-butadiene-styrene block copolymer (hereinafter which is abbreviated to SBS), styrene-butadiene rubber (hereinafter which is abbreviated to SBR), polysiloxane, or the like may be used. Of these rubber polymers, SIS, PIB, and polysiloxane are preferable, and SIS and PIB are more preferable. The adhesives may be used alone or as a mixture of two or more kinds.

A blending amount of the adhesive added is preferably from 5 to 90% by mass, more preferably from 10 to 70% by mass relative to the total mass of the adjuvant preparation. The case in which the blending amount of the adhesive added is adjusted to the range described above is preferable in terms of the permeation of the adjuvant preparation to skin or mucous membrane, and preferable in terms of the formation of the adhesive layer when a plaster is formed.

When the tackifying force is insufficient, it is desirable to separately add a tackifier resin. The tackifier resin may include rosin derivatives (e.g., rosin, glycerol ester of rosin, hydrogenated rosin, glycerol ester of hydrogenated rosin, pentaerythritol ester of rosin, and the like), alicyclic saturated hydrocarbon resins (e.g., ARKON P 100, Arakawa Chemical Industries, Led.), aliphatic hydrocarbon resins (e.g., Quintone B170, Zeon Corporation), terpene resins (e.g., Clearon P-125, Yasuhara Chemical Co., Ltd.), maleic acid resins, and the like. The glycerol esters of the hydrogenated rosin, the alicyclic saturated hydrocarbon resins, aliphatic hydrocarbon resin, and the terpene resins are particularly preferable.

A blending amount of the tackifier resin added is preferably from 5 to 70% by mass, more preferably from 5 to 60% by mass, even more preferably from 10 to 50% by mass relative to the total mass of the adjuvant preparation, considering a sufficient tackifying force as the plaster and an irritation to the skin when it is peeled off.

The plasticizer may include petroleum oil (e.g., liquid paraffin, paraffin process oil, naphthene process oil, aromatic process oil, and the like), squalane, squalene, plant oil (e.g., olive oil, *camellia* oil, castor oil, tall oil, peanut oil, and the like), silicon oil, dibasic acid esters (e.g., dibutyl phthalate, dioctyl phthalate, and the like), liquid rubber (e.g., liquid polybutene, liquid isoprene rugger, and the like), liquid fatty acid esters (isopropyl myristate, hexyl laurate, diethyl sebacate, diisopropyl sebacate, and the like), diethylene glycol, polyethylene glycol, glycol salicyltae, propylene glycol, dipropylene glycol, triacetin, triethyl citrate, crotamiton, and the like. Of the plasticizers, the liquid paraffin, liquid polybutene, isopropyl myristate, hexyl laurate, and diethyl sebacate are preferable, the liquid paraffin, liquid polybutene, and isopropyl myristate are more preferable. The plasticizers may be used alone or as a mixture of two or more kinds.

A blending amount of the plasticizer added is preferably from 10 to 70% by mass, more preferably from 10 to 60% by mass, even more preferably from 10 to 50% by mass relative to the total mass of the adjuvant preparation. The case in which the blending amount of the plasticizer added is adjusted to the range described above is preferable in terms of the permeation of the adjuvant preparation to the skin or mucous membrane, and the sufficient cohesive force can be maintained when the plaster is formed.

It is possible to use any compound which has hitherto been recognized to have an absorption promoting effect on the skin as the absorption accelerator. The absorption accelerator may include, for example, fatty acids, fatty alcohols, fatty acid ester, amides, ethers, aromatic organic acids, aromatic alcohols, aromatic organic acid esters or ethers, which have 6 to 20 carbon atoms (which may be saturated or unsaturated, or may be cyclic, linear, or branched), lactic acid esters, acetic acid esters, monoterpen compounds, sesquiterpen compounds, Azone, Azone derivatives, pyrothiodecane, glycerol fatty acid esters, propylene glycol fatty acid esters, sorbitan fatty acid esters (Span-type), polysorbates (Tween-type), polyethylene glycol fatty acid esters, polyoxyethylene hardened castor oil (HCO-type), polyoxyethylene alkyl ethers, sucrose fatty acid esters, vegetable oil, and the like. The absorption accelerators may be used alone or as a mixture of two or more kinds.

A binding amount of the absorption accelerator added is preferably from 0.01 to 40% by mass, more preferably from 0.05 to 10% by mass, even more preferably from 0.1 to 5% by mass relative to the total mass of the adjuvant preparation, considering the sufficient permeation to the skin, and the irritation to the skin such as flare or edema.

The adjuvant preparation may be used as various dosage form, and can be formed into the same dosage form as that of transdermal or transmucosal administration preparations which have been conventionally used. As the dosage form of the adjuvant preparation, dosage forms capable of transdermally or transmucosally administrating the adjuvant composition are preferable, and a dosage form such as an ointment, a cream, a gel, a suppository, a hydrogel patch preparation, a patch preparation, a lotion, a solution, an impregnated-type preparation, or a blister are preferable. The dosage forms of the patch preparation or the impregnated-type preparation are more preferable, and the dosage form of the impregnated-type preparation is even more preferable. When the preparation has such a dosage form, a non-invasive administration to the body can be performed as an adjuvant preparation for external dosage form.

The patch preparation may include a matrix-type tape preparation, a laminated-type tape preparation, and a reservoir-type patch preparation. Of these, the matrix-type tape preparation and the reservoir-type patch preparation are preferable, and the reservoir-type patch preparation is more preferable.

The matrix-type tape preparation refers to a tape preparation having an adhesive layer in which a pharmacologically active substance is dispersed and contained in a sticky base among the tape preparations. The matrix-type tape preparation has a support on one surface of the adhesive layer and a releasing liner on the other surface. The base may include a substantially rubber (vitrified) polymer or gel.

The laminated-type tape preparation refers to a tape preparation having multiple adhesive layers in which a pharmacologically active substance is dispersed and contained in a sticky base, each adhesive layer having a support on one surface thereof and a releasing liner on the other surface, among the tape preparations.

The reservoir-type patch preparation refers to a patch preparation having a reservoir to store a pharmacologically active substance wherein a backing member (support) impermeable to the medicine is disposed on one surface of the reservoir and a releasing liner, or a adhesive layer permeable to the medicine and the releasing liner are disposed on the other surface.

The impregnated-type preparation generally refers to a preparation obtained in a manner in which a pad is impregnated with a liquid agent containing an active component and holds it, and the resulting pad is covered with a sticky cover material. The structure is not particularly limited, and can contain a support, a backing member (a film) impermeable to the liquid agent, a sticky cover agent, a pad, a liner, and the like. When the impregnated-type preparation is formed, it is possible to stable hold the liquid agent, the ointment, or the gel with which the pad is impregnated. The impregnated-type preparation may be prepared in a manner in which the liquid agent is stored in a state in which it is held in a blister vessel, and a pad is impregnated with the liquid agent upon the administration.

As the pad, for example, a natural member such as pulp, a natural textile member such as gauze or absorbent cotton, a synthetic fiber textile such as polyester, polyethylene, or polyvinyl, or the like may be used. These members may be combined to process into a woven fabric or non-woven fabric, which may be used.

The adjuvant preparation may be formed into the dosage form described above, which may be applied to the skin or mucous membrane, and it is also possible to administrate to the skin or mucous membrane by a microneedle puncture, a needle-free injection, a skin abrading, or a mucous membrane abrading.

As the administration method of the adjuvant preparation, a method may be used in which at least a part of the microneedle is coated with the adjuvant preparation, and the administration is performed by the puncture. The coating to the microneedle can be performed in a manner described, for example, in Japanese Unexamined Patent Publication No. 2004-504120, Japanese Unexamined Patent Publication No. 2004-528900, or WO 2005/016440. The administration method of the adjuvant preparation may be an administration method by an iontophoresis, a sonophoresis, or an electroporation.

The antigen refers to a substance which binds to an antigen receptor on an immune cells and initiates an immunologic response. The antigen is not particularly limited. It is possible to use, for example, polynucleotide (DNA vaccine or RNA vaccine) a protein-based vaccine, or the like. The antigen may include, for example, attenuated and inactivated virus, such as cytomegalovirus, hepatitis B virus, hepatitis C virus, human papillomavirus, rubella virus, or varicella zoster; attenuated and inactivated bacterium, such as *Bordetella pertussis, Clostridium tetani, Corynebacterium diphtheriae*, group A *streptococcus, Legionella pneumophila, Neisseria meningitidis, Pseudomonas aeruginosa, Streptococcus pneumoniae, Treponema pallidum*, or *Vibrio cholerae*; protein, polysaccharide, oligosaccharide, lipoprotein, and mixture thereof.

It is also possible to use a commercially available vaccine containing an antigenic agonist. Such a vaccine may include, for example, influenza vaccine, Lyme disease vaccine, rabies vaccine, measles vaccine, mumps vaccine, varicella vaccine, smallpox vaccine, hepatitis vaccine, pertussis vaccine, diphtheria vaccine, and the like. Further, antigens used in a vaccine therapy of cancer, arteriosclerosis, neurological disease, Alzheimer's disease, and the like.

An allergen substance having antigenicity (sensitizing potential) may also be used as the antigen. The allergen substance is exemplified by various metals and chemical substances. In an allergy test to disclose an antigen of an atopic dermatitis and its treatment, house dust such as dust and inactivated mite and pollen may be used. The allergen substance may include antigens recognized by inflammatory T cells relating to T-cell mediated autoimmune diseases and symptoms.

The method for administrating the antigen is not particularly limited, and oral administration, administration by injection (intramuscular, subcutaneous, and intradermal), administration by microneedle puncture, transdermal or transmucosal administration may be used. In the case of transdermal administration, a transdermal administration means is selected according to the skin permeation of the antigen and the necessary administration amount. When the antigen can be transdermally administrated, transdermal noninvasive preparation containing the adjuvant composition and the antigen can be formed. When the antigen does not have sufficient transdermal or transmucosal activity, it may be non-transdermally or non-transmucosally administrated, and, for example, the injection administration or the oral administration can be considered. In the case of the injection administration, the adjuvant composition and the antigen may be administrated at the same time.

As the administration method of the adjuvant preparation, it is preferable to administrate the adjuvant preparation (particularly preferably the impregnated-type preparation and the patch preparation) before or after the non-transdermal or non-transmucosal administration (injection, microneedle puncture, or the like) of the antigen, or at the same time when the antigen is administrated. It is more preferable to administrate the adjuvant preparation after the antigen is non-transdermally or non-transmucosally administrated, and it is more preferable to administrate the adjuvant preparation immediately after the antigen is non-transdermally or non-transmucosally administrated. In that case, the administration of the adjuvant preparation (preferably the administration by plaster) can be continued while the antigen is administrated. For example, while the antigen is administrated by the microneedle puncture, the adjuvant preparation can be separately administrated by the plaster.

When the administration method of the adjuvant preparation is plaster, the pasting time is not particularly limited so long as the adjuvant preparation can sufficiently permeate the skin or mucous membrane and the effects thereof can be exhibited, and it is preferably from 0.1 to 96 hours, more preferably from 0.5 to 48 hours, even more preferably from 2 to 24 hours. The pasting time may be from 0.1 to 96 hours, from 0.5 to 96 hours, from 2 to 96 hours, from 4 to 96 hours, or from 6 to 96 hours, so long as it is within the range described above. The pasting time may also be from 0.1 to 48 hours, from 0.5 to 48 hours, from 2 to 48 hours, from 4 to 48 hours, or from 6 to 48 hours, so long as it is within the range described above. The pasting time may also be from 0.1 to 12 hours, from 0.5 to 12 hours, from 2.0 to 12 hours, or from 6 to 12 hours so long as it is within the range described above. Of these, it is more preferable that the lower limit of the pasting time is set longer, and it is more preferable that the upper limit of the pasting time is set shorter.

When a mixture of the antigen and the adjuvant composition or the adjuvant preparation is used, a blending ratio may be appropriately decided depending on the combination of the antigen and the adjuvant. It is preferable to blend them so that the adjuvant concentration is higher.

According to one aspect of the present invention, an immunostimulation method or an immunomodulation method using the adjuvant composition or the adjuvant preparation according to the present embodiment is provided. Such a method is excellent in increase of the immunogenicity of the antigen and increase of the antibody titer.

According to one aspect of the present invention, therefore, an immunostimulation method is provided which contains the step of transdermally or transmucosally administrating the adjuvant composition or the adjuvant preparation to an individual necessary for promoting the immunoreaction.

The individual necessary for promoting the immunoreaction includes, for example, an individual for prevention by the antigen administration, and an individual contracting a disease or disorder necessary for treatment by the antigen administration. The individual may be human. Here, the antigen includes viruses and bacteria which can be used as the antigen described above. The immunostimulation method or immunomodulation method can also be called as a method for prevention or treatment in a manner appropriate for a subject to be applied. For example, when the adjuvant composition or preparation is applied to an individual necessary for promoting an immunoreaction in order to prevent onset of a viral infection, the immunostimulation method or immunomodulation method can also be called as a method for preventing a viral infection.

In the immunostimulation method or immunomodulation method, it is possible to administrate the adjuvant composition or adjuvant preparation described above in an effective amount for an effective time through an effective route for inducing an effect of promoting a desired immunologic response or immunoreaction. For example, an effective amount of the adjuvant composition or adjuvant preparation may be administrated once, or administrated in several times.

In the immunostimulation method or immunomodulation method, the transdermal or transmucosal administration can be performed 1 to 5 times per day, and may be performed 1 to 3 times per day or once or twice per day.

In the immunostimulation method or immunomodulation method, the adjuvant composition or adjuvant preparation may be administrated at the same time when the antigen is administrated, or there may be a time difference between the administration thereof and the antigen administration. In the immunostimulation method or immunomodulation method, it is preferable to perform the administration of the adjuvant composition or adjuvant preparation through a different route from that of the administration of the antigen. A site to which the adjuvant composition or adjuvant preparation is administrated may be the same site or region to which the antigen is applied or a site or region different from the site to which the antigen is administrated.

In the immunostimulation method or immunomodulation method, with respect to an administration mode of the adjuvant composition or adjuvant preparation and an administration mode of the antigen, for example, a combination of the subcutaneous injection or microneedle puncture administration of the antigen, and the transdermal or transmucosal administration of the adjuvant composition or the like is preferable, and a combination of the microneedle puncture administration of the antigen and the transdermal administration of the adjuvant composition or the like is more preferable. When an administration device such as the microneedle is used, the adjuvant composition or the like of the present invention can be applied, while application of the administration device is continued.

The adjuvant composition or adjuvant preparation can be administrated to the intact skin or intact mucous membrane. In order to increase an absorption efficiency of the adjuvant composition or adjuvant preparation, the skin or mucous membrane is preferably subjected to a physical or chemical treatment.

As the physical or chemical treatment, at least one treatment selected from, for example, the group consisting of a heat-treatment (thermal treatment), an ultrasonic treatment, an electric field treatment, a magnetic field treatment, a pressure treatment, an alkali treatment, a laser irradiation, an abrading treatment, and a microneedle is preferable.

The immunologic response can be more safely completed with a higher efficiency by using a device of an iontophoresis, an electroporation, or a sonophoresis (ultrasonic waves), or a device on which a microcannula, a microneedle puncture, or a needleless injection is mounted. It is preferable to apply it to at least one of change, hydration, denaturation, pore formation, separation or bypass formation of a lamellar structure in a skin stratum corneum. When the administration of the adjuvant preparation is accompanied by the change, hydration, denaturation, pore formation, separation or bypass formation of the lamellar structure in the stratum corneum, the transdermal absorption of the adjuvant preparation can be more promoted.

A kit used in the immunostimulation method may utilize the adjuvant composition or adjuvant preparation described above. It is enough that the kit contains the adjuvant composition or adjuvant preparation, and the kit may further contain an antigen or a device for administrating the antigen. As the device for administrating the antigen, for example, a device for administration such as a microneedle or an injector can be used.

One embodiment of the kit may be, for example, a kit containing a microneedle at least a part of whose surface is coated with an antigen, and a patch preparation with which the adjuvant composition is impregnated.

It is considered that the langerhans' cells of the skin or mucous membrane are activated by transdermally or transmucosally administrating the adjuvant composition according to the present embodiment through the same or different administration of the antigen, and signals are efficiently transmitted from the skin or mucous membrane to TH cells existing in the lymph nodes, whereby a high immunologic response can be completed. From the above, a convenient evaluation of antigenicity in an external medicine, a cosmetics, or an allergen substance, prevention or treatment of an infectious disease, cancer, or an allergic disease by using a vaccine, and a treatment of a T-cell mediated autoimmune disease can be realized. The adjuvant composition and the adjuvant preparation according to the present embodiment greatly contribute to the development of the pharmaceutical industry and the related industries thereof.

EXAMPLES

The present invention is specifically explained by means of Examples, but the invention is not limited thereto.

Experimental Example 1

The solubility of lauryl alcohol in propylene glycol alone, glycerol alone, or a mixed solvent of propylene glycol and glycerol was evaluated. The lauryl alcohol was added to the solvent in a blending amount shown in Table 1, and the solubility at 20° C. was evaluated according to criteria described below. The results are shown in Table 1.

A: A case of complete dissolution

B: A case in which the solvent is semitransparent but is uniform.

C: A case of separation

TABLE 1

| Blending amount of lauryl alcohol (% by mass) | Solubility of lauryl alcohol | | | | | | | | | | |
|---|---|---|---|---|---|---|---|---|---|---|---|
| 0 | A (0/100) | A (10/90) | A (20/80) | A (30/70) | A (40/60) | A (50/50) | A (60/40) | A (70/30) | A (80/20) | A (90/10) | A (100/0) |
| 0.1 | B (0/100) | B (10/90) | A (20/80) | A (30/70) | A (40/60) | A (50/50) | A (60/40) | A (70/30) | — | — | — |
| 0.5 | — | C (10/90) | C (20/80) | C (30/70) | A (40/60) | A (50/50) | A (60/40) | A (70/30) | — | — | — |
| 1.0 | C (0/99) | C (10/89) | C (20/79) | C (30/69) | C (40/59) | A (49/50) | A (59/40) | A (69/30) | — | — | — |
| 3.0 | — | C (10/87) | C (19/78) | C (29/68) | C (39/58) | C (48/49) | B (58/39) | A (68/29) | A (78/19) | — | — |
| 5.0 | — | — | — | — | C (38/57) | C (47/48) | C (57/38) | A (66/29) | A (76/19) | — | A (95/0) |
| 10 | — | — | — | — | — | C (45/45) | C (54/36) | A (63/27) | A (72/18) | — | A (90/0) |
| 20 | — | — | — | — | — | C (40/40) | — | A (56/24) | A (64/16) | — | A (80/0) |
| 40 | — | — | — | — | — | C (30/30) | — | A (42/18) | A (48/12) | — | A (60/0) |
| 60 | — | — | — | — | — | — | — | C (28/18) | A (32/8) | A (36/4) | A (40/0) |
| 90 | — | — | — | — | — | — | — | C (7/3) | A (8/2) | A (9/1) | A (10/0) |

* In parentheses, a blending amount of propylene glycol/an amount of glycerol is shown.

Example 1

An adjuvant composition containing lauryl alcohol, propylene glycol, and glycerol in blending amounts (% by mass) shown in Table 2 was prepared. A Lint Cloth (Manufactured by Hakujuji Co., Ltd., cut into a 2 cm² round shape) with which 120 μL of the obtained adjuvant composition was impregnated was used as a sample for a skin irritation test.

[Skin Irritation Test]

The back of a female rabbit (JW) (SPF) was subjected to a hair-shearing and shaving treatment. After an acclimation term of 2 weeks, rabbits having a good systemic condition and a good skin conditions were selected, and the test was performed.

The sample for the skin irritation test described above was pasted to the back skin of the rabbit for 24 hours. After 0.5 hours, 24 hours, and 48 hours from the peeling off of the sample was peeled off, the skin responses were observed and evaluated in accordance with Draize standard. As the evaluation result, the test were performed using 2 to 6 rabbits as the subject in the same sample, and an average value of the measurement results was used. The evaluation results are shown in Table 2.

The Draize standard is a standard which is adopted for evaluation of a skin response. First, the skin condition of the test subject was visually observed from the viewpoints of formation of flare, scab, or edema, and the skin condition of the test subject was scored according to the following score criteria:

<Occurrence of Flare and Formation of Scab>
Point 0: No flare
Point 1: Very mild flare is observed (distinguishable with difficulty).
Point 2: Clear flare is observed.
Point 3: Moderate to strong flare is observed.
Point 4: High flare (red of a beet) is observed and formation of slight scab (damage in a deep part) is observed.
<Formation of Edema>
Point 0: No edema
Point 1: Very mild flare is observed (distinguishable with difficulty).
Point 2: Clear flare is observed.
Point 3: Moderate to strong flare is observed.
Point 4: High flare (red of a beet) is observed and formation of slight scab (damage in a deep part) is observed.

A total value (Primary Irritation Index, P.I.I. value) of the score obtained in the observation of the flare and the scab, and the score obtained in the observation of the edema formation was calculated, and the skin response was evaluated according to the following criteria:
<Draize Standard>
Mild Irritative Substance: P.I.I.≤2
Moderate Irritative Substance: 2<P.I.I.≤5
Strong Irritative Substance: 5<P.I.I.≤8

Examples 2 to 6, Reference Example 1, and Comparative Examples 1 to 6

An adjuvant composition was prepared and a sample for evaluation was produced in the same manner as in Example 1, except that the amounts of the lauryl alcohol, propylene glycol and glycerol added were changed to those shown in Table 2 or Table 3.

The obtained sample for evaluation was subjected to the skin irritation test in the same manner as in Example 1. The results are shown in Table 2 and Table 3. From Table 2 and Table 3 it was confirmed the tendency to show the skin irritation to be strong, when the content of lauryl alcohol is 40% by mass or more. It was confirmed that in the adjuvant compositions in Examples 4 to 6, having a lauryl alcohol content of 20% by mass or less, the skin irritation was moderate, which was sufficiently suppressed.

TABLE 2

|  | Example | | | | | | Reference Example |
|---|---|---|---|---|---|---|---|
|  | 1 | 2 | 3 | 4 | 5 | 6 | 1 |
| Lauryl alcohol | 5.0 | 10 | 20 | 5.0 | 10 | 20 | 40 |
| Propylene glycol | 95 | 90 | 80 | 76 | 72 | 64 | 60 |
| Glycerol | — | — | — | 19 | 18 | 16 | — |
| Propylene glycol/glycerol (ratio of content) | — | — | — | 4 | 4 | 4 | — |
| Skin irritation | moderate | moderate | moderate | moderate | moderate | moderate | moderate |
| P.I.I. value | 2.8 | 3.4 | 3.7 | 3.50 | 3.83 | 3.67 | 4.2 |

TABLE 3

|  | Comparative Example | | | | | |
|---|---|---|---|---|---|---|
|  | 1 | 2 | 3 | 4 | 5 | 6 |
| Lauryl alcohol | 70 | 100 | — | 40 | 60 | 80 |
| Propylene glycol | — | — | 100 | 48 | 32 | 16 |
| Glycerol | — | — | — | 12 | 8 | 4 |
| Propylene glycol/glycerol (ratio of content) | — | — | — | 4 | 4 | 4 |
| Skin irritation | strong | strong | weak | strong | strong | strong |
| P.I.I. value | 5.1 | 5.2 | 0.0 | 5.44 | 5.67 | 5.22 |

Example 7

An adjuvant composition containing lauryl alcohol and propylene glycol in blending amounts (% by mass) shown in Table 4 was prepared. A tape for impregnation was impregnated with 120 µL of the obtained adjuvant composition was used as a sample for evaluation. A laminate of a Lint Cloth (Manufactured by Hakujuji Co., Ltd., cut into a 2 cm²) and an acrylic tape was used as the tape for impregnation.

[Measurement of Immuno IgG Antibody Titer: Mouse Immunity Test]

The adjuvant composition was subjected to a mouse immunity test. Ovalbumin (OVA) antigen was administrated to an abdomen of a 7-week old female BALB-C mouse, and then the adjuvant composition was transdermally administrated.

The OVA antigen was administrated in an amount of 0.1 µg through an intradermal injection. The administration was performed using an aqueous solution prepared with physiological saline solution so that a concentration is 0.1 µg/50 µL.

After that, the adjuvant composition was administrated by pasting the sample for evaluation described above on the skin of the mouse for 6 hours. The sample for evaluation was fixed in any group using a Coban bandage and a Skinagate mesh. With respect of the administration of the antigen and the adjuvant composition, an additional administration was performed after 2 weeks in addition to an initial administration. In order to evaluate an OVA specific IgG antibody titer, blood collection was performed after 4 weeks. The OVA specific IgG antibody titer was measured by ELISA. The results are shown in Table 3.

Examples 8 to 19, Reference 2, and Comparative Examples 7 to 10

An adjuvant composition was prepared and a sample for evaluation was produced in the same manner as in Example 1, except that the amounts of the lauryl alcohol, propylene glycol and glycerol added were changed to those shown in Table 4 or Table 5.

The obtained sample for evaluation was subjected to the mouse immunity test in the same manner as in Example 7. The results are shown in Table 4 and Table 5.

TABLE 4

|  | Example |  |  |  |  |  |  |  |  |  |  |  |  | Reference Example |
|---|---|---|---|---|---|---|---|---|---|---|---|---|---|---|
|  | 7 | 8 | 9 | 10 | 11 | 12 | 13 | 14 | 15 | 16 | 17 | 18 | 19 | 2 |
| Lauryl alcohol | 0.5 | 1.0 | 3.0 | 20 | 1.0 | 1.0 | 1.0 | 1.0 | 3.0 | 5.0 | 20 | 20 | 20 | 40 |
| Propylene glycol | 99.5 | 99 | 97 | 80 | 89.1 | 79.2 | 69.3 | 49.5 | 57 | 66.5 | 72 | 64 | 56 | 60 |
| Glycerol | — | — | — | — | 9.9 | 19.8 | 29.7 | 49.5 | 40 | 28.5 | 8.0 | 16 | 24 | — |
| Propylene glycol/glycerol (ratio of content) | — | — | — | — | 9.0 | 4.0 | 2.3 | 1.0 | 1.4 | 2.3 | 9.0 | 4.0 | 2.3 | — |
| Immuno IgG antibody Titer (log 10) | 2.1 | 2.6 | 2.7 | 2.5 | 2.7 | 2.8 | 2.8 | 2.7 | 3.2 | 2.9 | 2.7 | 3.0 | 3.3 | 2.6 |
| Standard deviation | 0.3 | 0.2 | 0.3 | 0.8 | 0.4 | 0.6 | 0.5 | 0.3 | 0.1 | 0.4 | 0.5 | 0.4 | 0.2 | 0.1 |

TABLE 5

|  | Comparative Example |  |  |  |
|---|---|---|---|---|
|  | 7 | 8 | 9 | 10 |
| Lauryl alcohol | 100 | — | — | 0.1 |
| Propylene glycol | — | 100 | 70 | 69.9 |
| Glycerol | — | — | 30 | 30 |
| Propylene glycol/glycerol (ratio of content) | — | — | 2.3 | 2.3 |
| Immuno IgG antibody Titer (log 10) | 3.2 | 1.7 | 1.8 | 1.6 |
| Standard deviation | 0.5 | 0.9 | 1.0 | 0.9 |

As shown in Table 4 and Table 5, it was confirmed that the adjuvant compositions of Examples 7 to 19 exhibit the sufficient effect of potentiating the immunologic response.

From the above, it was shown that the adjuvant compositions of the present invention are more excellent in the safety and the effect of potentiating the immunologic response compared to the conventional adjuvant compositions. The adjuvant compositions of the present invention can be administrated separately from the antigen, and does not require a combination administration with the antigen, which is generally performed in other injection adjuvant compositions. The compositions of the present invention is particularly excellent in the respect in which after the antigen is administrated, the adjuvant preparation containing a high concentration of the adjuvant composition is administrated by pasting or coating to the skin or mucous membrane, whereby the desired effect can be obtained. It was also shown that the skin irritation is further suppressed compared to cases using conventional impregnated-type preparation, and the increase of the immuno IgG antibody titer can be safely attained.

The invention claimed is:
1. An adjuvant composition for transdermal or transmucosal administration, comprising lauryl alcohol, propylene glycol, and glycerol,
    wherein contents of the lauryl alcohol, the propylene glycol, and the glycerol are 0.5 to 20% by mass, 49 to 90% by mass, and 8.0 to 50% by mass, relative to the total mass of the adjuvant composition, respectively,
    wherein the lauryl alcohol is dissolved in the propylene glycol and glycerol, and
    wherein a ratio of the content of the propylene glycol to the content of the glycerol is from 1.0 to 9.0.
2. The adjuvant composition according to claim 1, wherein a ratio of the content of the propylene glycol to the content of the lauryl alcohol is from 1.0 to 99.
3. An adjuvant preparation, comprising the adjuvant composition according to claim 1.
4. The adjuvant preparation according to claim 3, wherein a content of the adjuvant composition is 50 to 100% by mass relative to the total mass of the adjuvant preparation.
5. The adjuvant preparation according to claim 3, which is an ointment, a cream, a gel, a suppository, a hydrogel patch preparation, a patch preparation, a lotion, a solution, an impregnated-type preparation, or a blister.
6. The adjuvant preparation according to claim 5, wherein the patch preparation is a matrix-type tape preparation, a laminated-type tape preparation, or a reservoir-type patch preparation.
7. The adjuvant preparation according to claim 3, which is administrated to a skin or a mucous membrane by microneedle puncture, needle-free injection, skin abrading, or mucous membrane abrading.
8. The adjuvant preparation according to claim 3, wherein at least a part of the microneedle is coated with the adjuvant preparation, and which is administrated to a skin or a mucous membrane by puncture.
9. The adjuvant preparation according to claim 3, which is administrated by iontophoresis, sonophoresis, or electroporation.
10. The adjuvant preparation according to claim 3, which is administrated to an intact skin, an intact mucous membrane, a skin that had been subjected to physical or chemical treatment, or a mucous membrane that had been subjected to physical or chemical treatment.
11. The adjuvant preparation according to claim 10, wherein the physical or chemical treatment is at least one treatment selected from the group consisting of a heat-treatment, an ultrasonic treatment, an electric field treatment, a magnetic field treatment, a pressure treatment, an alkali treatment, a laser irradiation, an abrading treatment, and a microneedle treatment.

12. The adjuvant preparation according to claim 3, which is administrated to the skin or mucous membrane either before the administration of an antigen or after the administration of an antigen.

13. A kit comprising the adjuvant composition according to claim 1.

14. The kit according to claim 13, further comprising an apparatus for an antigen or an antigen administration.

* * * * *